(12) United States Patent
Uematsu et al.

(10) Patent No.: US 7,183,261 B2
(45) Date of Patent: Feb. 27, 2007

(54) GALACTOSYLCERAMIDE ANALOGS, AND β-GLUCOCEREBROSIDASE ACTIVATORS, EXTERNAL SKIN PREPARATIONS AND METHOD OF ACTIVATING β-GLUCOCEREBROSIDASE USING THE ANALOGS

(75) Inventors: Rie Uematsu, Ebetsu (JP); Fumio Nakajima, Osaka (JP); Masahiro Yoshida, Kuwana (JP); Kyoko Fukunaga, Odawara (JP); Mariko Hara, San Francisco, CA (US); Shintaro Inoue, Odawara (JP); Shinichiro Nishimura, Sapporo (JP)

(73) Assignee: Kao Corporation, Tokyo (JP)

( * ) Notice: Subject to any disclaimer, the term of this patent is extended or adjusted under 35 U.S.C. 154(b) by 54 days.

(21) Appl. No.: 10/482,110

(22) PCT Filed: Jun. 27, 2002

(86) PCT No.: PCT/JP02/06532

§ 371 (c)(1),
(2), (4) Date: Dec. 24, 2003

(87) PCT Pub. No.: WO03/002584

PCT Pub. Date: Jan. 9, 2003

(65) Prior Publication Data

US 2004/0242499 A1    Dec. 2, 2004

(30) Foreign Application Priority Data

Jun. 28, 2001    (JP)    ............................. 2001-196016

(51) Int. Cl.
*A01N 43/04*    (2006.01)
*A61K 31/70*    (2006.01)
*C07H 15/00*    (2006.01)
*C07H 17/00*    (2006.01)

(52) U.S. Cl. ........................... 514/23; 514/24; 514/25; 536/4.1; 536/17.2; 536/17.6; 536/18.7; 536/53; 536/54

(58) Field of Classification Search .............. 536/1.11, 536/4.1, 18.7, 17.2, 17.6, 53, 54; 554/1; 514/23, 24, 25
See application file for complete search history.

(56) References Cited

FOREIGN PATENT DOCUMENTS

| JP | 5-186491 A | | 7/1993 |
|---|---|---|---|
| JP | 5-202085 | * | 8/1993 |
| JP | 5-202085 A | | 8/1993 |
| JP | 8-116971 | * | 5/1996 |
| JP | 8-116971 A | | 5/1996 |
| WO | WO 95/25736 | * | 9/1995 |
| WO | WO 95/25736 A1 | | 9/1995 |

OTHER PUBLICATIONS

Faroux-Corlay et al., Synthesis of Single- and Double-Chain Fluorocarbon and Hydrocarbon Galactosyl Amphiphiles and their anti-HIV-1 Activity, Carbohydrate Research, vol. 327, issue 3, pp. 223-260, Jul. 2000.*
Sasaki et al., "Synthesis of Novel Galactosyl Ligands for Liposomes and the Influence of the Spacer on Accumulation in the Rat Liver", Biological and Pharmeucitical Bulletin, vol. 18, No. 5, pp. 740-746, May 1995.*
P.D. Mier et al., "Lysosomal Hydrolases of the Epidermis", British Journal of Dermatology, vol. 95, 1976, pp. 271-274.
B. Faroux-Corlay et al., "Synthesis of Single- and Double-Chain Fluorocarbon and Hydrocarbon Galactosyl Amphiphiles and their anti-HIV-1 Activity", Carbohydrate Research, vol. 327, Issue 3, Jul. 24, 2000, pp. 223-260.
A. Sasaki et al., "Syntheses of Novel Galactosyl Ligands for Liposomes and the Influence of the Spacer on Accumulation in the Rat Liver", Biological & Pharmaceutical Bulletin, vol. 18, No. 5. May 5, 1995, pp. 740-746.
Hara, M. et al., "Galactocerebroside and Not Glucocerebroside or Ceramide Stimulate Epidermal β-Glucocerebrosidase Activity," Journal of Dermatological Science, Jan. 1998, vol. 16, No. 2, pp. 111-119.

* cited by examiner

Primary Examiner—Shaojia Anna Jiang
Assistant Examiner—Traviss C. McIntosh, III
(74) Attorney, Agent, or Firm—Foley & Lardner LLP

(57) ABSTRACT

Galactosylceramide analogues represented by the following formula (1) or (2).

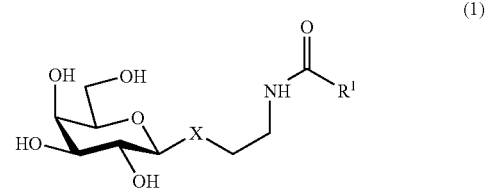

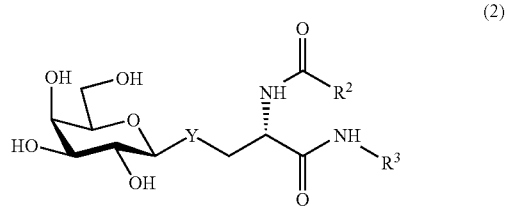

(wherein X and Y each represent S or O, $R^1$ and $R^2$ each represent an alkyl group or an alkenyl group each having 9 to 35 carbon atoms. $R^3$ represents an alkyl group or an alkenyl group each having 2 to 30 carbon atoms.)

It is provided a β-glucocerebrosidase activator which is easily available, and external skin preparations and a method of activating β-glucocerebrosidase, in which improvement in formation of horny layer transmission barrier is expected by activating β-glucocerebrosidase so that an improved effect in rough skin is also expected.

8 Claims, 3 Drawing Sheets

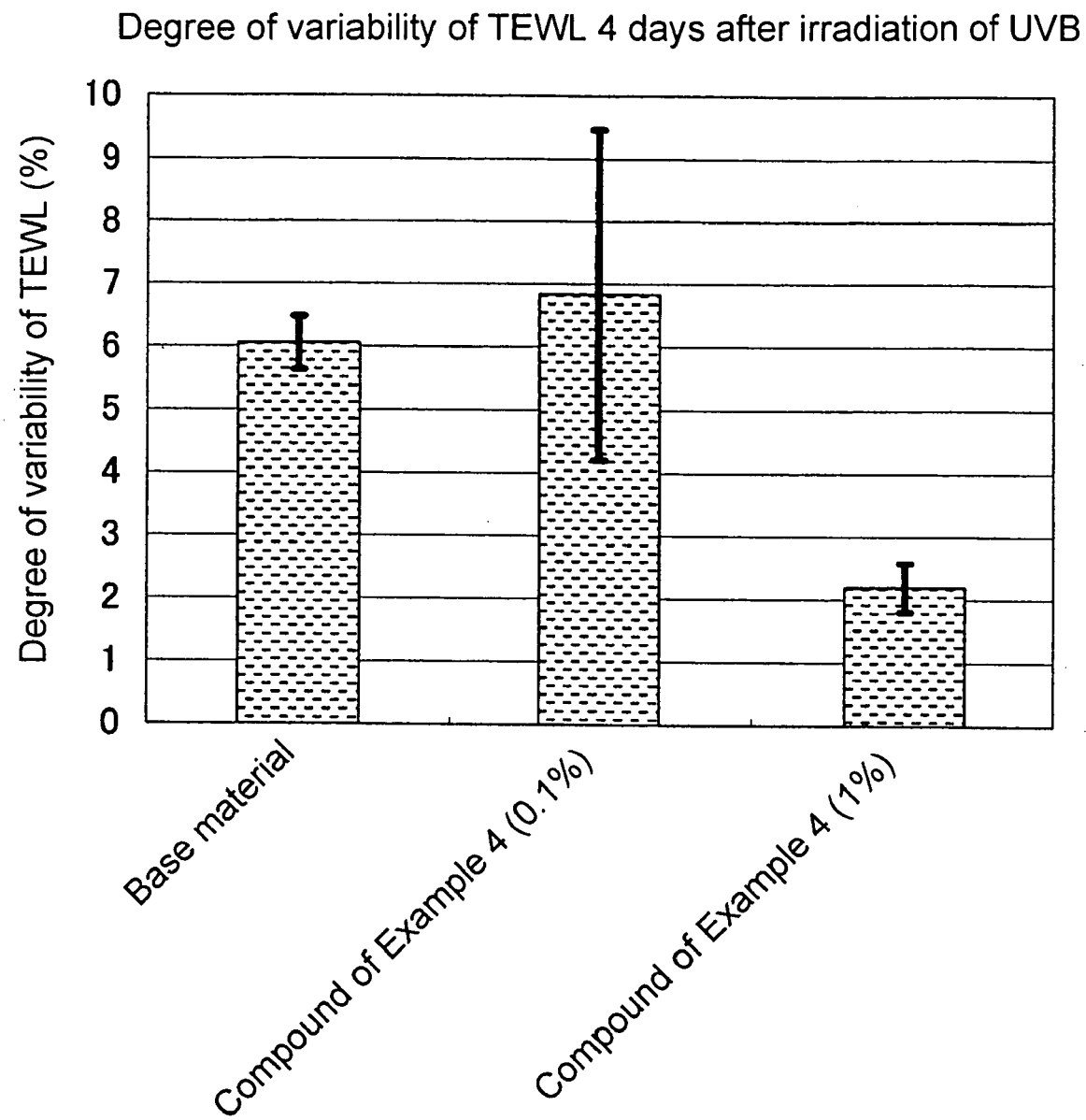

GALACTOSYLCERAMIDE ANALOGS, AND β-GLUCOCEREBROSIDASE ACTIVATORS, EXTERNAL SKIN PREPARATIONS AND METHOD OF ACTIVATING β-GLUCOCEREBROSIDASE USING THE ANALOGS

Novel galactosylceramide analogues, and β-glucocerebrosidase activator, external skin preparations and method of activating β-glucocerebrosidase using the same

TECHNICAL FIELD

The present invention relates to novel galactosylceramide analogues, and a β-glucocerebrosidase activator, external skin preparations and a method of activating β-glucocerebrosidase using the same. More specifically, it relates to a β-glucocerebrosidase activator to activate a β-glucocerebrosidase in epidermis by a specific galactosylceramide analogues, external skin preparations and a method of activating β-glucocerebrosidase, and improvements in rough skin and various kinds of skin diseases can be expected by these.

BACKGROUND ART

Rough skin (dry skin) generally means skin with scaling in a dry state in stratum corneum(S.C.). Such a rough skin occurs due to dissolution of S.C. lipids such as cholesterol, ceramide, fatty acid, etc., and degeneration of corneocytes caused by ultraviolet rays, detergents, etc. or hypoplasia of epidermal permeability barrier due to disintegration of a balance between proliferation and keratinization of keratinocytes or the like. For the puropose of preventing or treating the rough skin, it has been carried out rearches to feed S.C. lipids or its analogues, or to administer a substance controlling proliferation and keratinization of keratinocytes such as epidermal growth factor (EGF), etc.

This S.C. lipids biosynthesized in cells of a spinous layer and granular layer are released to intercellular directly under the S.C., and extended and spread to take a lamellar (lamella) structure. Lamellar granules are constituted by glucosylceramide, cholesterol, ceramide, phospholipids, etc., and substantially no glucosylceramide was contained in S.C. lipids. That is, it can be considered that glucosylceramide in lamellar granules is hydrolyzed by β-glucocerebrosidase and converted into ceramide, and the ceramide has a lamella structure, so that it improves formation of the epidermal peameability barrier as the S.C. lipids, whereby it has a barrier function of preventing from rough skin. For example, in a patient of Type 2 Gaucher's disease in which β-glucocerebrosidase had been genetically and completely defected, morbid rough skin has been observed, and according to histological research on the epidermis, abnormality in lamella structure of S.C. lipids has been admitted. Also, in transgenic mouse in which β-glucocerebrosidase had artificially defected, a correlation between abnormality in a lamella structure of S.C. lipids and rough skin has been admitted. Moreover, when β-glucocerebrosidase is inhibited, rough skin and abnormality in a lamella structure of S.C. lipids have been experimentally observed. From these various facts, it has been suggested that for formation of normal epidermal permeability barrier, it is necessary that the glucosylceramide is hydrolyzed by β-glucocerebrosidase to ceramide. Accordingly, by activating β-glucocerebrosidase, it can be considered that formation of the epidermal permeability barrier can be improved, and as a result, rough skin can be recovered.

Under such a background, as an activator of β-glucocerebrosidase, it has heretofore been known SAP-2 found from guinea pig spleen or Ala or Saposin C found from human Gaucher's disease spleen.

However, these activation factors are proteins and there are great problems to activate β-glucocerebrosidase in epidermis by external application in the points of epidermal absorption and safety. Also, it is extremely difficult to utilize these proteins by isolation for industrial purpose in view of an economical aspect.

On the other hand, as a β-glucocerebrosidase activator other than proteins, β-galactosylceramide has been known.

However, β-galactosylceramide actually applicable is derived from extracts of bovine brain, and to use it externally involves a great problem in the point of safety. Also, it is extremely difficult to synthesize β-galactosylceramide with a large amount and it is expensive, so that these are defects for utilizing it industrially.

Accordingly, an object of the present invention is to provide a β-glucocerebrosidase activator which is easily available, and external skin preparations and a method of activating β-glucocerebrosidase, in which improvement in formation of epidermal permeability barrier is expected by activating β-glucocerebrosidase so that an improved effect in rough skin is also expected.

DISCLOSURE OF THE INVENTION

Thus, the present inventors have earnestly studied about a method of solving the prior art problems in view of the above-mentioned circumstance, and as a result, they have found that β-glucocerebrosidase in surface skin can be unexpectedly activated extremely easily and strongly by the compounds specifically mentioned hereinbelow whereby accomplished the present invention.

That is, the present invention relates to galactosylceramide analogues represented by the following formula (1) or (2), a β-glucocerebrosidase activator, external skin preparations and a method of activating β-glucocerebrosidase using the same.

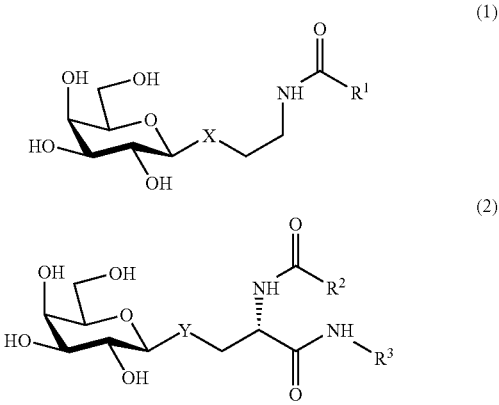

(wherein X and Y each represent S or O, $R^1$ and $R^2$ each represent an alkyl group or an alkenyl group each having 9 to 35 carbon atoms. $R^3$ represents an alkyl group or an alkenyl group each having 2 to 30 carbon atoms.)

BRIEF DESCRIPTION OF THE DRAWINGS

FIG. 3 is a drawing showing a result (result of Test example 2) of an effect of coating the compound of Example 4 to rough surface due to UVB.

BEST MODE FOR CARRYING OUT THE INVENTION

Figure 1:
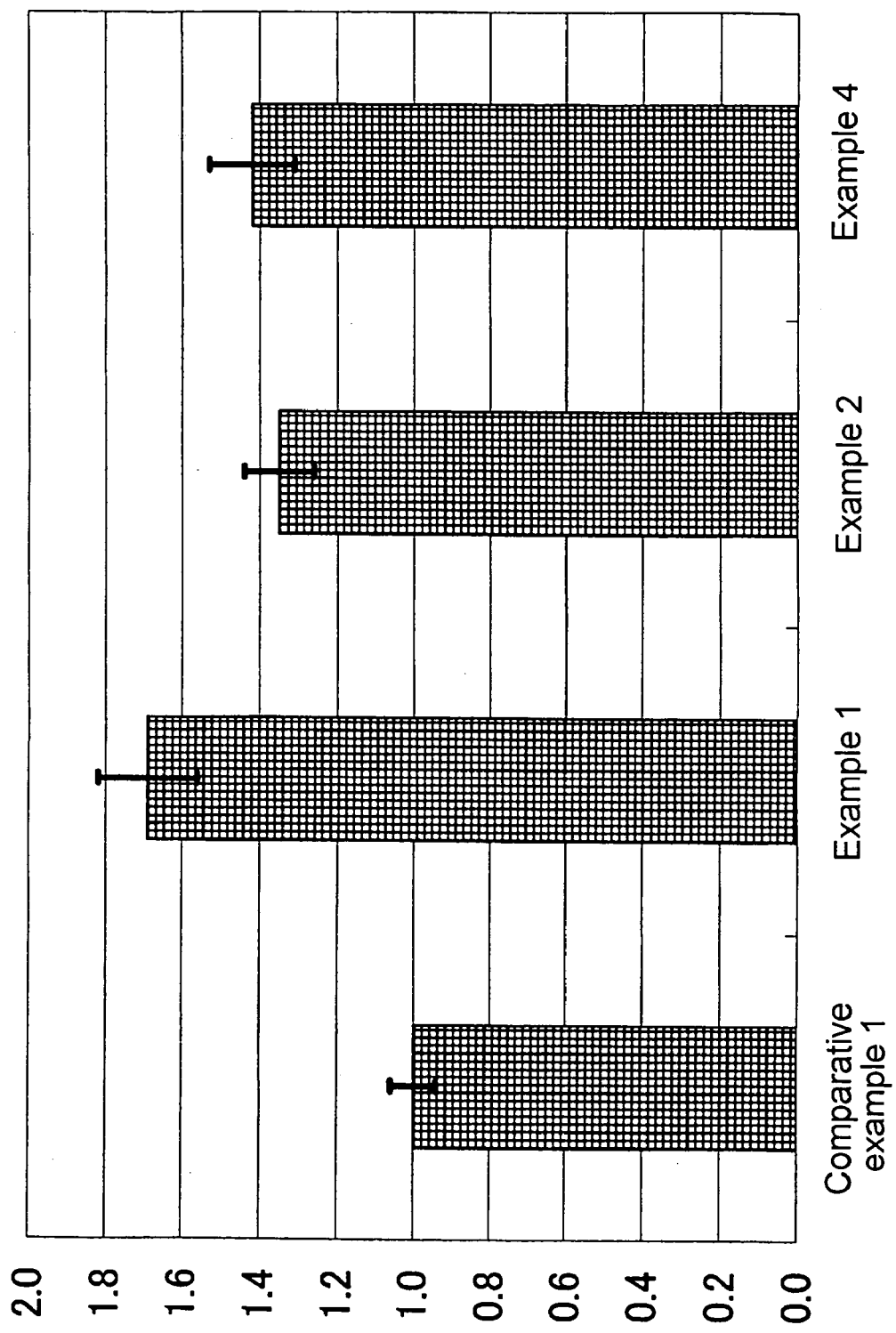
FIG. 1 is a drawing showing a result of a measurement test (Test example 1) of activating ability of β-glucocerebrosidase on epidermic cells.

The galactosylceramide analogues to be used in the present invention are represented by the above-mentioned formula (1) or (2). X and Y each represent a sulfur atom or an oxygen atom, and preferably a sulfur atom in view of the effects. $R^1$ and $R^2$ each have 9 to 35 carbon atoms, preferably 14 to 22, most preferably 16 to 20 carbon atoms. $R^3$ has 2 to 30 carbon atoms, preferably 14 to 22 carbon atoms, most preferably 6 to 14 carbon atoms. Also, $R^1$, $R^2$ and $R^3$ may be either saturated or unsaturated. More specifically, those represented by the following chemical formulae (3) to (6) may be mentioned.

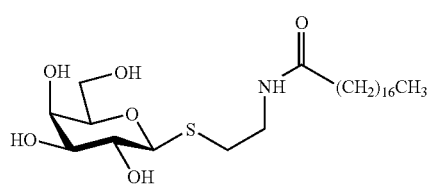
(3)

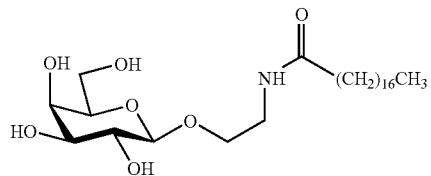
(4)

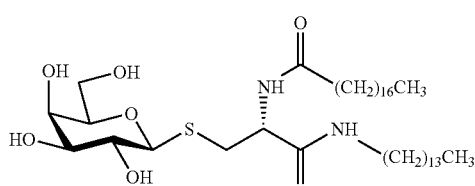
(5)

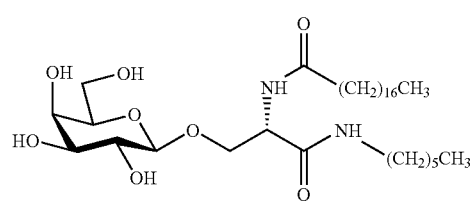
(6)

These compounds can be easily prepared by the conventionally known amide synthesis method. For example, when an outline of the synthesis method is shown, the compound represented by the formula (2) having two alkyl chains can be produced by introducing galactose into an amine, serine into which a carboxylic acid portion has been protected or cysteine by a glycosilation reaction, introducing an alkyl group by deprotection of the amino group portion and condensation reaction, subsequently removing the protective group for the carboxylic acid, reacting phosphorus trichloride to prepare an acid chloride, and then, reacting with a primary amine. Also, the compound represented by the formula (1) having a single chain compound can be produced in the same manner.

The β-glucocerebrosidase activator according to the present invention is a composition containing one or more kinds of the galactosylceramide analogues represented by the above-mentioned formula (1) or (2) as an effective ingredient for treating rough skin.

The β-glucocerebrosidase activator and external skin preparations according to the present invention can be made various preparations such as ointment, lotion, emulsion, milk, poultice, pack, mist, foam, granules, powder, gel and the like. Incidentally, in the present invention, the external skin preparations are intended to be applied to all skins of a body including head skin and also include a bath agent. The base material is not specifically limited so long as it is an external base material generally used. Also, the final form may be made cosmetic, medicament or quasi-drug.

A formulation amount of the galactosylceramide analogues in the β-glucocerebrosidase activator or the external skin preparations is preferably 0.005 to 5.0% by weight, more preferably 0.01 to 3.0% by weight based on the total weight of the composition. If the formulation amount is less than 0.005% by weight, there is a case where the effect objected by the present invention is sometimes insufficient, while if it exceeds 5.0% by weight, there is a case where an improved effect in accordance with an increased amount thereof cannot sometimes be obtained.

EXAMPLES

In the following, the invention is explained in detail by referring to Examples. Incidentally, the present invention is not limited by the following Examples.

Example 1

Preparation of N-[2-β-D-galactopyranosylthio-1-(tetradecylcarbamoyl) ethyl]octadecanoylamide [Compound of the formula (5)]

(1) In 4 mL of chloroform were dissolved 300 mg of 1,2,3,4,6-penta-O-acetyl-β-D-galactopyranoside and 430 mg of methyl 2-(benzyloxycarbonylamino)-3-mercaptopropionate, and after cooling the solution to 0° C., 1.3 mL of boron trifluoride diethyl ether complex was added thereto and the resulting mixture was stirred at room temperature for 20 hours. Chloroform was added to the reaction mixture, and the resulting mixture was washed with a saturated aqueous sodium hydrogen carbonate solution and a saturated saline solution. The residue was purified by preparative thin layer chromatography (Eluent; n-hexane:ethyl acetate=3:2) to obtain 370 mg of methyl 2-(benzyloxycarbonylamino)-3-(2,3,4,6-tetra-O-acetyl-β-D-galactopyranosylthio)propionate.

(2) In a mixed solvent comprising 5 mL of 1,4-dioxane and 5 mL of methanol was dissolved 370 mg of methyl 2-(benzyloxycarbonylamino)-3-(2,3,4,6-tetra-O-acetyl-β-D-galactopyranosylthio) propionate, 200 mg of 20% palladium carbon hydroxide was added to the solution, and the mixture was stirred under hydrogen stream for 18 hours. Insoluble materials were filtered off by using Cellite™, and the filtrate was concentrated under reduced pressure. The residue was dissolved in 6 mL of DMF, and 193 mg of stearic acid, 180 mg of EDC [; 1-ethyl-3-(3-dimethylaminopropyl)-carbodiimide] and 140 mg of HOBT (; 1-hydroxybenzotriazole) were added to the solution and the resulting mixture was stirred at room temperature overnight.

The reaction mixture was extracted with ethyl acetate, washed with 2 mol/L of hydrochloric acid and a saturated aqueous sodium hydrogen carbonate solution, the ethyl acetate layer was dried over anhydrous magnesium sulfate, and then, the solvent was removed under reduced pressure. The finally obtained residue was purified by medium pressure column chromatography (Eluent; n-hexane:ethyl acetate=4:1) to obtain 313 mg of methyl 2-(octadecanoylamino)-3-(2,3,4,6-tetra-O-acetyl-β-D-galactopyranosylthio)propionate.

(3) In 6 mL of pyridine was dissolved 313 mg of methyl 2-(octadecanoylamino)-3-(2,3,4,6-tetra-O-acetyl-β-D-galactopyranosylthio)propionate, 515 mg of lithium iodide was added to the solution and the resulting mixture was refluxed under nitrogen atmosphere for 4 hours. The reaction mixture was extracted with ethyl acetate, washed with 2 mol/L of hydrochloric acid, the ethyl acetate layer was dried over anhydrous magnesium sulfate, and then, the solvent was removed under reduced pressure. The finally obtained residue was purified by medium pressure column chromatography (Eluent; chloroform:methanol=15:1) to obtain 247 mg of 2-(octadecanoylamino)-3-(2,3,4,6-tetra-O-acetyl-β-D-galactopyranosylthio) propionic acid.

(4) In 4 mL of DMF was dissolved 247 mg of 2-(octadecanoylamino)-3-(2,3,4,6-tetra-O-acetyl-β-D-galactopyranosylthio)-propionic acid, and 80 mg of n-tetradecylamine, 100 mg of EDC and 80 mg of HOBT were added to the solution, and the resulting mixture was stirred at room temperature for 17 hours. The reaction mixture was extracted with ethyl acetate, washed with 2 mol/L of hydrochloric acid and a saturated aqueous sodium hydrogen carbonate solution, the ethyl acetate layer was dried over anhydrous magnesium sulfate, and then, the solvent was removed under reduced pressure. The finally obtained residue was purified by medium pressure column chromatography (Eluent; n-hexane: ethyl acetate=3:1) to obtain 278 mg of N-[1-(tetradecylcarbamoyl)-2-(2,3,4,6-tetra-O-β-D-galactopyranosylthio)-ethyl]octadecanoylamide.

(5) In a mixed solvent comprising 5 mL of THF and 5 mL of methanol was dissolved 278 mg of N-[1-(tetradecylcarbamoyl)-2-(2,3,4,6-tetra-O-β-D-galactopyranosylthio)ethyl]-octadecanoylamide, 28% sodium methylate methanol solution was added to the solution with a catalytic amount, and the resulting mixture was stirred at room temperature for one hour. The reaction mixture was neutralized by using cation exchange resin (Dowex™50-X8), the resin was filtered off, and the filtrate was concentrated under reduced pressure. The finally obtained residue was crystallized from methanol to obtain 202 mg of N-[2-(β-D-galactopyranosylthio)-1-(tetradecylcarbamoyl)ethyl]octadecanoylamide as white crystal.

NMR (DMSO-$D_6$) δ: 0.86 (t, 3H, J=5.9 Hz), 1.24 (s, 46H), 1.35–1.55 (m, 4H), 2.15–2.50 (m, 2H), 3.71 (bs, 1H), 4.24 (dt, 1H), 7.71 (bt, 1H), 7.92 (d, 1H, J=7.9 Hz).

TOF-MS: m/z 768(M+Na)$^+$, 784(M+K)$^+$.

Elemental analysis value (as $C_{41}H_{80}N_2O_7S \cdot 1/10 H_2O$) Calculated value (%) C, 65.93; H, 10.82; N, 3.75; S, 4.29. Found value (%) C, 65.67; H, 10.82; N, 3.68; S, 4.29.

Example 2

Preparation of N-[2-(β-D-galactopyranosyloxy)ethyl]octadecanoylamide [Compound of the formula (4)]

(1) In 10 mL of 1,2-dichloroethane were dissolved 1.8 g of 1,2,3,4,6-penta-O-acetyl-β-D-galactopyranoside and 1.2 g of 2-(benzyloxycarbonylamino)ethanol, and after cooling the mixture to 0° C., 3.6 mL of boron trifluoride diethyl ether complex was added to the mixture and the resulting mixture was stirred at room temperature for 17 hours. Chloroform was added to the reaction mixture, and the resulting mixture was washed with a saturated aqueous sodium hydrogen carbonate solution and a saturated saline solution. The residue was purified by silica gel chromatography (Eluent; n-hexane:ethyl acetate=3:1) to obtain 1.3 g of benzyl 2-(2,3,4,6-O-tetra-benzoyl-β-D-galactopyranosyloxy)ethylcarbamate.

(2) In a mixed solvent comprising 3 mL of 1,4-dioxane and 3 mL of methanol was dissolved 250 mg of benzyl 2-(2,3,4,6-O-tetra-benzoyl-β-D-galactopyranosyloxy)ethylcarbamate, and tetra-benzoyl-β-D-galactopyranosyloxy)ethylcarbamate, and 170 mg of 20% palladium carbon hydroxide was added to the solution and the resulting mixture was stirred under hydrogen stream for 18 hours. Insoluble materials were filtered off by using Cellite™, and the filtrate was concentrated under reduced pressure. The residue was dissolved in 5 mL of DMF, and 123 mg of stearic acid, 90 mg of EDC and 75 mg of HOBT were added to the solution, and the resulting mixture was stirred at room temperature overnight. The reaction mixture was extracted with ethyl acetate, washed with 2 mol/L of hydrochloric acid and a saturated aqueous sodium hydrogen carbonate solution, the ethyl acetate layer was dried over anhydrous magnesium sulfate, and then, the solvent was removed under reduced pressure. The finally obtained residue was purified by silica gel column chromatography (Eluent; n-hexane:ethyl acetate=1:1) to obtain 103 mg of N-[2-(2,3,4,6-tetra-O-benzoyl-β-D-galactopyranosyloxy)ethyl]octadecanoylamide.

(3) In a mixed solvent comprising 2 mL of 1,4-dioxane and 2 mL of methanol was dissolved 103 mg of N-[2-(2,3,4,6-tetra-O-benzoyl-β-D-galactopyranosyloxy)ethyl]octadecanoylamide, 28% sodium methylate methanol solution was added to the solution with a catalytic amount, and the resulting mixture was stirred at room temperature for 4 hours. The reaction mixture was neutralized by using cation exchange resin (Dowex™ 50-X8), the resin was filtered off, and then, the solvent was removed under reduced pressure. The finally obtained residue was crystallized from methanol to obtain 59 mg of N-[2-(β-D-galactopyranosyloxy)ethyl]octadecanoylamide as white crystal.

NMR (DMSO-$D_6$) δ: 0.84 (t, 3H, J=6.4 Hz), 1.26 (s, 28H), 1.45–1.50 (m, 2H), 2.04 (t, 2H, J=7.5 Hz), 3.40–3.50 (m, 3H), 3.61 (bs, 1H), 3.68 (dt, 1H, J=5.8, 10.2 Hz), 4.05 (d, 1H, J=6.7 Hz), 4.32, 4.56, 4.67, 4.81 (4bs, 4H), 7.72 (t, 1H, J=5.6 Hz).

TOF-MS: m/z 512 (M+Na)$^+$, 528 (M+K)$^+$.

Elemental analysis value (as $C_{26}H_{51}NO_7 \cdot 1/5 H_2O$): Calculated value (%) C, 63.31; H, 10.50; N, 2.84 Found value (%) C, 63.14; H, 10.22; N, 2.86.

Example 3

Preparation of N-[2-(β-D-galactopyranosylthio)ethyl]octadecanoylamide [Compound of the formula (3)]

(1) In a mixed solvent comprising 10 mL of methanol and 10 mL of 1,4-dioxane was dissolved 1.0 g of benzyl 2-(2,3,4,6-tetra-O-benzoyl-β-D-galactopyranosylthio)ethylcarbamate, 1 g of palladium hydroxide was added to the solution, and the resulting mixture was stirred under hydrogen stream for 6 hours. Insoluble materials were filtered off by using Cellite™, and the filtrate was concentrated under reduced pressure. The residue was dissolved in 10 mL of DMF, and 432 mg of stearic acid, 364 mg of EDC and 257 mg of HOBT were added to the solution, and the resulting mixture was stirred at room temperature overnight. The reaction mixture was diluted with chloroform, washed with 2 mol/L of hydrochloric acid and a saturated aqueous sodium hydrogen carbonate solution, the chloroform layer was dried over anhydrous magnesium sulfate, and then, the solvent was removed under reduced pressure. The finally obtained residue was purified by silica gel column chromatography (Eluent; n-hexane:ethyl acetate=3:1) to obtain 442 mg of N-[2-(2,3,4,6-tetra-O-benzoyl-β-D-galactopyranosylthio)-ethyl]octadecanoylamide.

(2) In a mixed solvent comprising 10 mL of 1,4-dioxane and 15 mL of methanol was dissolved 440 mg of N-[2-(2,3,4,6-tetra-O-benzoyl-β-D-galactopyranosylthio)ethyl]octadecanoylamide, 28% sodium methylate methanol solution was added to the solution with a catalytic amount, and the resulting mixture was stirred at room temperature for 2 hours. The reaction mixture was neutralized by using cation exchange resin (Dowex™ 50-X8), the resin was filtered off, and the filtrate was concentrated under reduced pressure. The finally obtained residue was crystallized from methanol to obtain 209 mg of N-[2-(β-D-galactopyranosylthio)ethyl] octadecanoylamide as white crystal.

NMR (DMSO-$D_6$) δ: 0.85 (t, 3H, J=6.6 Hz), 1.26 (s, 30H), 1.45–1.50 (m, 2H), 2.00–2.10 (t, 2H, J=7.2 Hz), 2.55–2.70 (m, 2H), 3.20–3.25 (m, 2H), 3.30–3.40 (m, 2H), 3.45–3.50 (m, 2H), 3.68 (bs, 1H), 4.20 (d, 1H, J=9.0 Hz), 4.37 (d, 1H, J=4.8 Hz), 4.55 (d, 1H, J=5.4 Hz), 4.76 (d, 1H, J=5.4 Hz), 4.92 (d, 1H, J=5.4 Hz), 7.84 (bt, 1H).

TOF-MS: m/z 528 $(M+Na)^+$, 544 $(M+K)^+$.

Elemental analysis value (as $C_{26}H_{51}NO_6S$): Calculated value (%) C, 61.75; H, 10.16; N, 2.77; S, 6.34. Found value (%) C, 61.65; H, 10.10; N, 2.77; S, 6.35.

Example 4

Preparation of N-[2-(β-D-galactopyranosyloxy)-1-(hexylcarbamoyl)ethyl]octadecanoylamide [Compound of the formula (6)]

(1) In 35 mL of chloroform were dissolved 2.4 g of benzyl 2-(2,3,4,6-tetra-O-benzoyl-β-D-galactopyranosylthio)ethylcarbamate and 1 g of methyl 3-hydroxy-2-(octadecanoylamino)propionate, and after cooling the solution to 0° C., 1.4 g of N-iodosuccinimide and 0.13 mL of trifluoromethanesulfonic acid were added to the solution and the resulting mixture was stirred at room temperature for 3 hours. Then, chloroform was added to the reaction mixture, and the resulting mixture was washed with a saturated aqueous sodium hydrogen carbonate solution and 10% aqueous sodium thiosulfate solution. The chloroform layer was dried over anhydrous magnesium sulfate, magnesium sulfate was filtered off, and the filtrate was concentrated under reduced pressure. The residue was purified by silica gel chromatography (Eluent; n-hexane:ethyl acetate=3:1) to obtain 1.4 g of methyl 2-(octadecanoylamino)-3-(2,3,4,6-tetra-O-benzoyl-β-D-galactopyranosyloxy)propionate.

(2) In 26 mL of pyridine was dissolved 1.4 g of methyl 2-(octadecanoylamino)-3-(2,3,4,6-tetra-O-benzoyl-β-D-galactopyranosyloxy)propionate, 1.7 g of lithium iodide was added to the solution, and the resulting mixture was refluxed under nitrogen atmosphere for 4 hours. Chloroform was added to the reaction mixture, the resulting mixture was washed with 2 mol/L of hydrochloric acid, the chloroform layer was dried over anhydrous magnesium sulfate, and then, the solvent was removed under reduced pressure. The finally obtained residue was purified by silica gel chromatography (Eluent; chloroform: methanol=60:1) to obtain 940 mg of 2-(octadecanoylamino)-3-(2,3,4,6-tetra-O-benzoyl-β-D-galactopyranosyloxy) propionic acid.

(3) In 10 mL of DMF was dissolved 940 mg of 2-(octadecanoylamino)-3-(2,3,4,6-tetra-O-benzoyl-β-D-galactopyranosyloxy)propionic acid, and 120 mg of n-hexylamine, 285 mg of EDC and 201 mg of HOBT were added to the solution, and the resulting mixture was stirred at room temperature for 4 hours. Chloroform was added to the reaction mixture, the resulting mixture was washed with 2 mol/L of hydrochloric acid and a saturated aqueous sodium hydrogen carbonate solution, the chloroform layer was dried over anhydrous magnesium sulfate, and then, the solvent was removed under reduced pressure. The finally obtained residue was purified by silica gel column chromatography (Eluent; n-hexane:ethyl acetate=3:1) to obtain 295 mg of N-[1-(hexylcarbamoyl)-2-(2,3,4,6-tetra-O-benzoyl-β-D-galactopyranosyloxy)ethyl]octadecanoylamide.

(4) In a mixed solvent comprising 5 mL of 1,4-dioxane and 5 mL of methanol was dissolved 290 mg of N-[1-(hexylcarbamoyl)-2-(2,3,4,6-tetra-O-benzoyl-β-D-galactopyranosyloxy)-ethyl]octadecanoylamide, 28% sodium methylate methanol solution was added to the solution with a catalytic amount, and the resulting mixture was stirred at room temperature for 3 hours. The reaction mixture was neutralized by using cation exchange resin (Dowex™ 50-X8), the resin was filtered off, and the filtrate was concentrated under reduced pressure. The finally obtained residue was crystallized from distilled water to obtain 144 mg of N-[2-(β-D-galactopyranosyloxy)-1-(hexylcarbamoyl)ethyl]octadecanoylamide as white crystal.

NMR (DMSO-$D_6$) δ: 0.85 (t, 6H, J=6.0 Hz), 1.24(s, 34H), 1.30–1.40 (m, 2H), 1.40–1.50 (m, 2H), 2.10–2.15 (m, 2H), 3.00–3.10 (m, 2H), 3.34 (t, 1H, J=6.6 Hz), 3.45–3.55 (m, 3H), 3.62 (bs, 1H), 3.89 (dd, 1H, J=4.8, 10.2 Hz), 4.07 (d, 1H, J=7.2 Hz), 4.35 (d, 1H, J=4.8 Hz), 4.40 (dt, 1H, J=5.4, 7.8 Hz), 4.55 (t, 1H, J=5.4 Hz), 4.69 (d, 1H, J=5.4 Hz), 4.85 (d, 1H, J=3.6 Hz), 7.67 (t, 1H, J=5.4 Hz), 7.85 (d, 1H, J=8.4 Hz).

TOF-MS: m/z 639 $(M+Na)^+$, 655$(M+K)^+$.

Elemental analysis value (as $C_{33}H_{64}N_2O_8$): Calculated value (%) C, 64.25; H, 10.46; N, 4.54. Found value (%) C, 64.02; H, 10.32; N, 4.55.

Test Example 1 Measurement Test of Activation Ability of β-Glucocerebrosidase for Epidermic Cells (1) Method (a) Cultured Epidermic Cells As human normal epidermic keratinocytes, those commercially available (Epidercell™: available from KURABO INDUSTRIES LTD.) were used.

(b) Medium for Cell Culture

As a medium, Medium 154S (available from KURABO INDUSTRIES LTD.) was used, and an additive HKGS (available from KURABO INDUSTRIES LTD.) to be added thereto was used as a growth factor.

(c) Preparation of Hepes Buffer Solution

In purified water were dissolved 7.15 g of Hepes, 1.8 g of glucose, 0.22 g of potassium chloride, 7.7 g of sodium chloride and 0.27 g of disodium hydrogen phosphate 12 hydrate, and after adjusting a pH to 7.4 with 1 mol/L of an aqueous sodium hydroxide solution, the total amount was made 1L.

(d) Cell Culture

Cell number of human normal epidermic cells was adjusted to $2.5 \times 10^4$/mL by Medium 154S, and each 4 mL of which was sowed to 60 mM of collagen coat plate (Falcon, trade name, available from Becton, Dickinson and Company), and it was subjected to static culture under an atmosphere of 95% air (V/V)–5% carbon dioxide gas (V/V) at 37° C. for 4 days.

Culture supernatant was removed by suction, and each 4 mL of Medium 154S to which each 200 μmol/L ethanol solution of the respective chemicals prepared in the above-mentioned Examples 1, 2 and 4 was so added that a final concentration of 5 μmol/L was added to the respective dishes. These dishes were subjected to static culture under an atmosphere of 95% air (V/V)–5% carbon dioxide gas (V/V) at 37° C. for 4 days. Also, ethanol alone containing no galactosylceramide analogues was used as Comparative example 1.

(e) Extraction of Crude Enzyme Solution

Culture supernatant was removed by suction, the residue was washed twice with 1 mL of phosphate buffered physiological saline solution, and the cells were scraped from dishes by a cell scraper (available from Sumitomo Bakelite Co., Ltd.). To the scraped cells was added 0.1 mmol/L phenylmethylsulfonyl fluoride-containing phosphate buffered physiological saline solution, crushed with an ultrasonic wave treatment device (available from Sonics and Materials Inc.), and supernatant by centrifugation was recovered as a crude enzyme solution.

(f) Measurement of β-Glucocerebrosidase Activity

It was measured according to the method of Miel and Van den Hurk (British Journal of Dermatology, vol. 95, pp. 271–274, 1976). That is, to 50 μL of the crude enzyme solution were added 500 μL of 100 mmol/L citric acid-200 mmol/L phosphate buffer solution (pH 5.6) and 500 μL of 10 mmol/L taurocholic acid-100 mmol/L citric acid-200 mmol/L phosphate buffer solution (pH 5.6), and the mixture was heated at 37° C. for 10 minutes. Then, 50 μL of 0.5 mmol/L 4-methylumbellifer-β-D glucoside (available from Sigma Co.) was added to the mixture and heated at 37° C. for 60 minutes. Thereafter, 200 mmol/L sodium carbonate-sodium hydrogen carbonate buffer solution (pH 10.5) was added to the mixture, and fluorescent strength was measured with an excitation wavelength of 360 nM and an absorption wavelength of 450 nM. Enzyme activity was calculated from a calibration curve prepared by fluorescent strength of 4-methylumbelliferone (available from Sigma Co.) as a standard material.

(2) Results

As shown in FIG. 1, in all of N-[2-(β-D-galactopyranosyloxy)ethyl]octadecanoylamide [Example 2; compound represented by the formula (4)], N-[2-β-D-galactopyranosylthio-1-(tetradecylcarbamoyl)ethyl]octadecanoylamide [Example 1; compound represented by the formula (5)] and N-[2-(β-D-galactopyranosyloxy)-1-(hexylcarbamoyl)ethyl] octadecanoylamide [Example 4; compound represented by the formula (6)], β-glucocerebrosidase activation effects were admitted.

Test Example 2 Rough Skin Recovery Test with Mouse (1) Method (a) Experimental Animals Hair-less mice with 5 mice per group with 9-weeks old at the time of initiating the test were used.

(b) Measurement Device and Conditions

Transepidermal water loss (in the following, abbreviated to as TEWL) was measured as follows by using a continuous sweat measurement device Hydrograph AMU-100 (available from K and E Inc.). A capsule with 1 square centimeter was contacted to skin, a nitrogen gas was introduced into the capsule (300 mL/min), water vapor contents was measured in the nitrogen gas before feeding to the capsule and after recovery from the capsule. From the difference between these values, a water content (mg/cm$^2$) vaporized from 1 square centimeter of the skin per minute was calculated, and it was defined to be TEWL.

(c) Samples and Experimental method

By using a base material (propylene glycol:ethanol=3:7), the compound of Example 4 [the compound represented by the formula (6)] was adjusted to a concentrations of 0.1% and 1.0%. Each 0.05 mL of the samples after the adjustment was coated onto a back skin of hair-less mouse (2.5 cm in diameter) in which TEWL had been previously measured once a day, with a frequency of 5 times per week for continuous 4 weeks. Thereafter, at the $3^{rd}$ day from the final coating of the coating before coating, 0.15 J/CM$^2$ of ultra-violet B wavelength (UVB) was once irradiated. TEWLs before irradiation of UVB, and 3 and 4 days after the irradiation were measured and compared in terms of a ratio with the TEWL before coating the base material.

(2) Results

Figure 2:
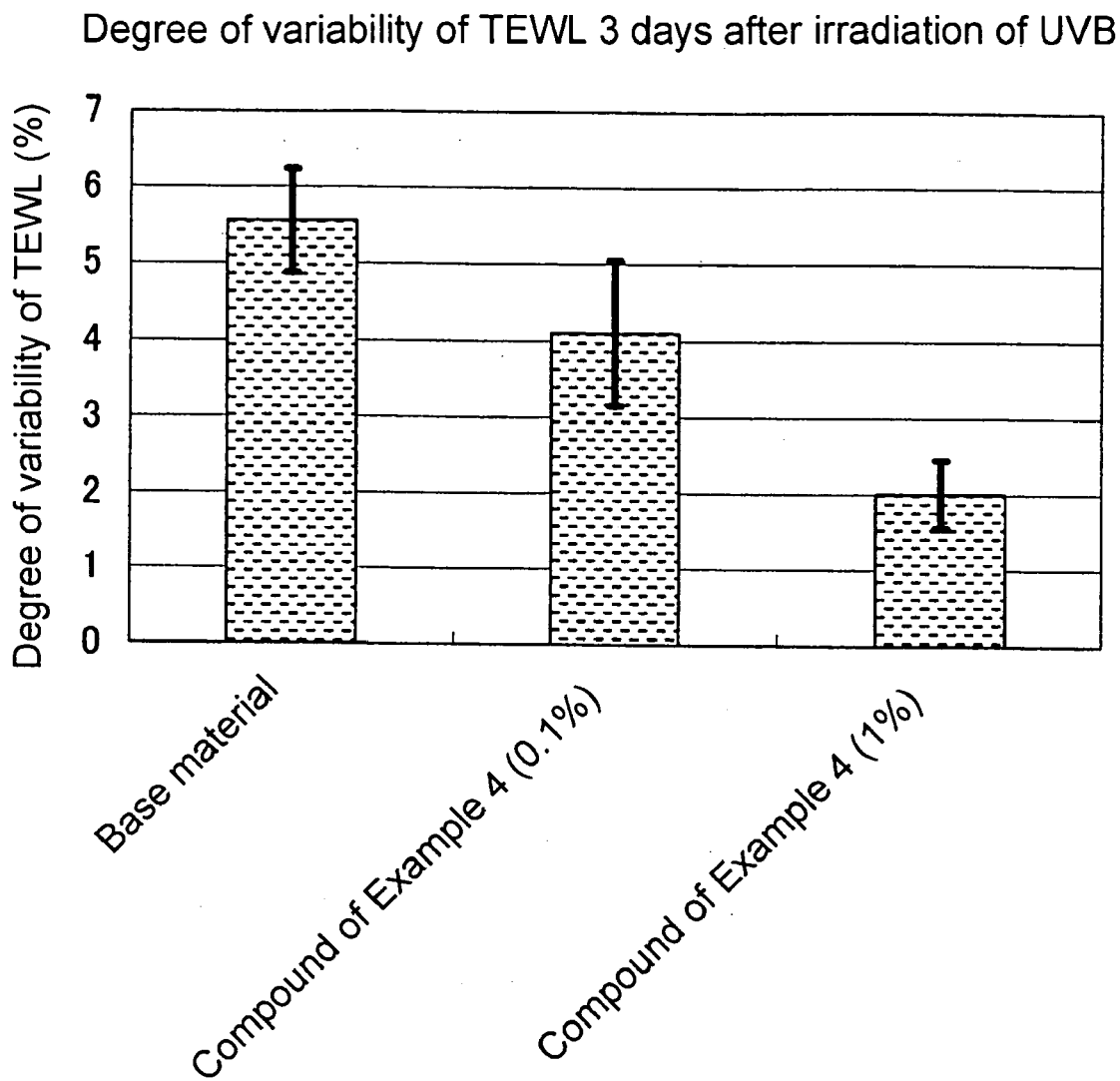
FIG. 2 is a drawing a result (result of Test example 2) of an effect of coating the compound of Example 4 to rough surface due to UVB.

As shown in FIG. 2 and FIG. 3, in N-[2-(β-D-galactopyranosyloxy)-1-(hexylcarbamoyl)ethyl]octadecanoylamide [the compound of Example 4; the compound represented by the formula (6)] at a concentration of 1.0%, a value of TEWL was significantly reduced as compared to that using a base material alone with a level of significance of p<0.01 (Dunnett's multiple comparison), and rough skin was recovered.

Example 5

Each 10 g of a 10% ethanol solution containing galactosylceramide analogues obtained in Examples 1 to 4 was heated to 80° C. with a hot water bath, and the following mixed components were added to prepare four kinds of each 100 g of lotions.

| | |
|---|---|
| Lactic acid | 0.3 g |
| Sodium citrate | 0.1 g |
| Glycerin | 2.0 g |
| Antiseptic, perfume and surfactant | Suitable amount |
| Purified water | Reminder up to 100 g in total |

INDUSTRIAL APPLICABILITY

As described above, it would be clear that the present invention can provide a β-glucocerebrosidase activator for surface skin which is capable of synthesizing simply and easily. Also, according to the present invention, it is possible to prophylaxis and prevention of rough surface as well as improvement of various kinds of skin diseases.

What is claimed is:

1. A method, of activating β-glucocerebrosidase in a body comprising applying compositions including more than 1 molecule of the same compound of formula (1) or (2) to the skin of a body, (1)

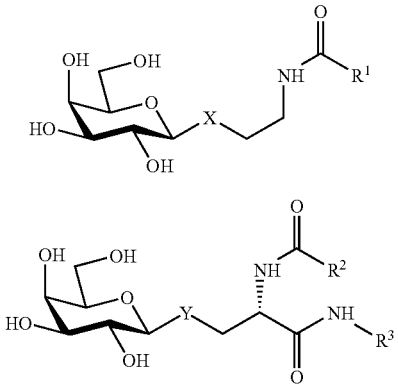

(2)

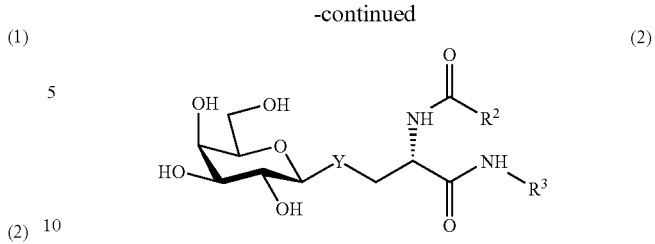

wherein X and Y each represent S or O, $R^1$ and $R^2$ each represent an alkyl group or alkenyl group each having 9 to 35 carbon atoms, and $R^3$ represents an alkyl group or an alkenyl group each having 2 to 30 carbon atoms.

wherein X and Y each represent S or O, $R^1$ and $R^2$ each represent an alkyl group or alkenyl group each having 9 to 35 carbon atoms, and $R^3$ represents an alkyl group or an alkenyl group each having 2 to 30 carbon atoms.

2. A method of activating β-glucocerebrosidase in a body according to claim 1, wherein X and Y each represent S or O, $R^1$ and $R^2$ each represent an alkyl group or alkenyl group each having 16 to 20 carbon atoms, and $R^3$ represents an alkyl group or an alkenyl group each having 6 to 14 carbon atoms.

3. A method of activating β-glucocerebrosidase in a body according to claim 1, wherein a composition containing the galactosylceramide analogues represented by the formula (1) or (2) in an amount of 0.005 to 5% by weight is used.

4. A method of activating β-glucocerebrosidase in a body according to claim 1, wherein a composition containing the galactosylceramide analogues represented by the formula (1) or (2) in an amount of 0.01 to 3% by weight is used.

5. A method of activating β-glucocerebrosidase in a body with scaling in stratum corneum comprising applying a composition including more than 1 molecule of the same compound of formula (1) or (2) to the skin with scaling in stratum corneum of a body;

(1)

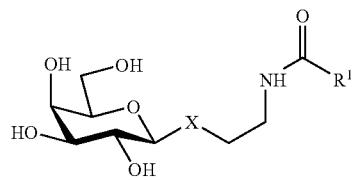

6. A compound of formula (3)

(3)

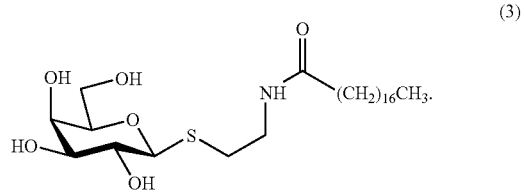

7. A compound formula (5)

(5)

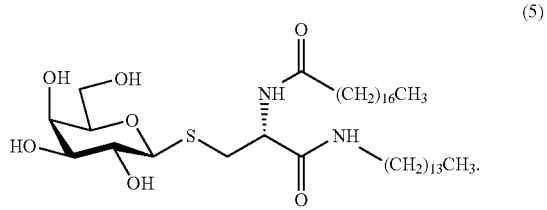

8. A compound of formula (6)

(6)

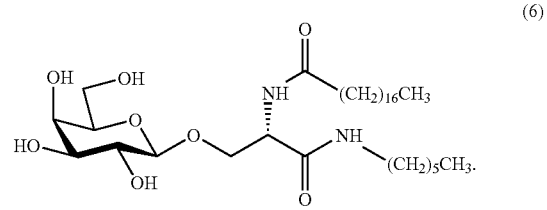

* * * * *

UNITED STATES PATENT AND TRADEMARK OFFICE
CERTIFICATE OF CORRECTION

PATENT NO. : 7,183,261 B2 Page 1 of 1
APPLICATION NO. : 10/482110
DATED : February 27, 2007
INVENTOR(S) : Uematsu et al.

It is certified that error appears in the above-identified patent and that said Letters Patent is hereby corrected as shown below:

On the title page,

[*] Notice: Subject to any disclaimer, the term of this patent is extended or adjusted under 35 USC 154(b) by (54) days Delete the phrase "by 54 days" and insert --by 109 days--

Signed and Sealed this

Eighth Day of July, 2008

JON W. DUDAS
*Director of the United States Patent and Trademark Office*